US011274305B2

(12) United States Patent
Howell et al.

(10) Patent No.: US 11,274,305 B2
(45) Date of Patent: Mar. 15, 2022

(54) COMPOSITIONS AND METHODS FOR IN VIVO EXCISION OF HIV-1 PROVIRAL DNA

(71) Applicants: United States Government as Represented by The Department of Veterans Affairs, Washington, DC (US); TRUSTEES OF DARTMOUTH COLLEGE, Hanover, NH (US)

(72) Inventors: Alexandra L. Howell, Lyme, NH (US); Susan K. Eszterhas, Plainfield, NH (US)

(73) Assignees: TRUSTEES OF DARTMOUTH COLLEGE, Hanover, NH (US); United States Government as Represented by The Department of Veterans Affairs, Washington, DC (US)

( * ) Notice: Subject to any disclaimer, the term of this patent is extended or adjusted under 35 U.S.C. 154(b) by 0 days.

(21) Appl. No.: 14/782,297

(22) PCT Filed: Mar. 25, 2014

(86) PCT No.: PCT/US2014/031674
§ 371 (c)(1),
(2) Date: Oct. 2, 2015

(87) PCT Pub. No.: WO2014/165349
PCT Pub. Date: Oct. 9, 2014

(65) Prior Publication Data
US 2016/0040165 A1 Feb. 11, 2016

Related U.S. Application Data

(60) Provisional application No. 61/808,437, filed on Apr. 4, 2013.

(51) Int. Cl.
C12N 15/113 (2010.01)
C12N 15/11 (2006.01)
A61K 31/7105 (2006.01)
A61K 38/17 (2006.01)

(52) U.S. Cl.
CPC ...... *C12N 15/1132* (2013.01); *A61K 31/7105* (2013.01); *A61K 38/1709* (2013.01); *C12N 15/111* (2013.01); *C12N 2320/30* (2013.01)

(58) Field of Classification Search
CPC ................................. C12N 2310/20
See application file for complete search history.

(56) References Cited

U.S. PATENT DOCUMENTS

| | | |
|---|---|---|
| 5,527,895 A | 6/1996 | Hampel et al. |
| 5,856,188 A | 1/1999 | Hampel et al. |
| 5,858,785 A | 1/1999 | Hampel et al. |
| 5,866,701 A | 2/1999 | Hampel et al. |
| 5,869,339 A | 2/1999 | Hampel et al. |
| 6,221,661 B1 | 4/2001 | Hampel et al. |
| 2005/0042620 A1* | 2/2005 | Hampel ............... C12N 15/113 435/6.12 |
| 2010/0076057 A1 | 3/2010 | Sontheimer et al. |
| 2010/0172881 A1* | 7/2010 | Hauber ............... C12N 15/1058 424/93.7 |
| 2012/0052483 A1 | 3/2012 | Opdyke et al. |
| 2014/0179770 A1* | 6/2014 | Zhang .................. C12N 15/86 514/44 R |

FOREIGN PATENT DOCUMENTS

JP 2016-501531 A 1/2016
WO 2014093622 A2 6/2014

OTHER PUBLICATIONS

Schroder et al. (2002) HIV-1 Integration in the Human Genome Favors Active Genes and Local Hotspots. Cell, 110:521-529.*
Mcintyre et al. (2009) 96 shRNAs designed for maximal coverage of HIV-1 variants. Retrovirology, 6(55):pp. 1-15.*
AF324493.2 (HIV-1 vector pNL4-3, NCBI Reference Sequence, priority to May 24, 2010, 7 pages).*
Cong et al. (2013) Multiplex Genome Engineering Using CRISPR/Cas Systems. Science, 339:819-823, and supplementary materials, published online Jan. 3, 2013.*
Mali et al. (2013) RNA-Guided Human Genome Engineering via Cas9. Science, 339:823-826.*
Makarova (2011) Evolution and classification of the CRISPR-Cas systems. Nature Reviews Microbiology, 9(6):467-477 (Year: 2011).*
Zetsche et al. (2015) Cpf1 Is a Single RNA-Guided Endonuclease of a Class 2 CRISPR-Cas System. Cell, 163:759-771 (Year: 2015).*
Shmakov et al. (2015) Discovery and Functional Characterization of Diverse Class 2 CRISPR-Cas Systems. Cell, 60:385-397 (Year: 2015).*
Ebina et al. (2013) Harnessing the CRISPR/Cas9 system to disrupt latent HIV-1 provirus. Scientific Reports, 3:2510, pp. 1-7 (Year: 2013).*
Mali et al. (2013) RNA-Guided Human Genome Engineering via Cas9. Science, 339:824-826, and supplementary data, published online Jan. 3, 2013 (Year: 2013).*
Mali et al. 'RNA-guided human genome engineering via Cas9, Science, Jan. 3, 2013, vol. 339, pp. 823-826.
Jinek et al. 'A programmable dual-RNA-guided DNA endonuclease in adaptive bacterial immunity,' Science, Jun. 28, 2012, vol. 337, pp. 816-821.
Wang Brian. 'RNA Guided Human Gene and Genome Engineering and Radical life extension, disease prevention and cures,' Jan. 12, 2013. Retrieved from Internet <http://nextbigfuture.com/2013/01/rna-guided-human-gene-and-genome.html> on Aug. 4, 2014.

(Continued)

*Primary Examiner* — Neil P Hammell
(74) *Attorney, Agent, or Firm* — Ballard Spahr LLP

(57) ABSTRACT

Methods and kits for excising HIV-1 DNA in vivo are provided, which employ Clustered Regularly Interspaced Short Palindromic Repeats (CRISPR) and CRISPR-Associated (cas) proteins. Vectors harboring nucleic acids encoding one or more guide RNA, wherein said guide RNA hybridizes with a target HIV-1 DNA are also provided.

10 Claims, 4 Drawing Sheets
Specification includes a Sequence Listing.

(56) References Cited

OTHER PUBLICATIONS

Cho et al., "Targeted genome engineering in human cells with the Cas9 RNA-guided endonuclease", Nat Biotechnol. (2013) 31(3):230-232. doi: 10.1038/nbt.2507. Epub Jan. 29, 2013, in 14 pages.
Habu et al., "Inhibition of HIV-1 gene expression by retroviral vector-mediated small-guide RNAs that direct specific RNA cleavage by tRNase ZL", Nucleic Acids Res. (2005)33(1):235-43. Print 2005, in 9 pages.
Extended European Search Report dated Dec. 16, 2016 for related European Patent Application No. 14779556.1, in 11 pages.
Karn et al., "Transcriptional and posttranscriptional regulation of HIV-1 gene expression", Cold Spring Harb Perspect Med. Feb. 2012;2(2):a006916. doi: 10.1101/cshperspect.a006916, in 18 pages.
Communication pursuant to Article 94(3) EPC dated Apr. 3, 2018 for related European Patent Application No. 14779556.1, in 8 pages.
Notice of Reasons for Rejection dated Feb. 26, 2018 for related Japanese Patent Application No. 2016-506325, in 10 pages.
Second Notice of Reasons for Rejection issued in co-pending Japanese Application No. 2016-506325 dated Sep. 14, 2018 in 8 pages.
Habu, et al., "Inhibition of HIV-1 gene expression by retroviral vector-mediated small-guide RNAs that direct specific RNA cleavage by tRNase ZL", Nucleic Acids Research, 2005, vol. 33, p. 235-243.
Karn et al., "Transcriptional and posttranscriptional regulation of HIV-1 gene expression", Cold Spring Harbor Perspectives in Medicine, Feb. 2012; 2(2): a006916.
Mali et al., "RNA-Guided Human Genome Engineering via Cas9", Science, Feb. 15, 2013, vol. 339, p. 823-826.
Office Action was filed on May 13, 2019 by the Japanese Patent Office for JP Application No. 2016-506325, which was filed on Mar. 25, 2014 and published as JP 2016514479, on May 23, 2016 (Applicant—United States Department of Veterans Affairs) (Original—4 pages/Translation—4 pages).

* cited by examiner

COMPOSITIONS AND METHODS FOR IN VIVO EXCISION OF HIV-1 PROVIRAL DNA

REFERENCE TO SEQUENCE LISTING

The Sequence Listing submitted Sep. 17,2021 as a text file named "37759_0180U1 Sequence Listing.txt," created on Sep. 16, 2021, and having a size of 18,419 bytes is hereby incorporated by reference pursuant to 37 C.F.R. § 1.52(e)(5).

INTRODUCTION

This application claims the benefit of priority from U.S. Provisional Application Ser. No. 61/808,437, filed Apr. 4, 2013, the content of which is incorporated herein by reference in its entirety.

This invention was made with government support under Grant No. 001 awarded by the Veteran's Administration. The government has certain rights in the invention.

BACKGROUND

The CRISPR (Clustered Regularly Interspaced Short Palindromic Repeat); SPIDR (Spacers Interspersed Direct Repeats), VNTR (Variable Number of Tandem Repeats), SRVR (Short Regularly Variable Repeats), or SRSR (Short Regularly Spaced Repeats) loci, described by Jansen et al. ((2002) *OMICS J. Integr. Biol.* 6:23-33), constitute a novel family of repeat sequences that is present in Bacteria and Archaea but not in Eukaryotes. The repeat loci are typically composed of repetitive stretches of nucleotides with a length of 25 to 37 base pairs alternated by nonrepetitive DNA spacers of approximately equal length.

The primary products of the CRISPR loci appear to be short RNAs that contain the invader targeting sequences, and are termed prokaryotic silencing RNAs (psiRNAs) based on their role in the pathway (Makarova, et al. (2006) *Biol. Direct* 1:7; Hale, et al. (2008) *RNA* 14:2572-2579). RNA analysis indicates that CRISPR locus transcripts are cleaved within the repeat sequences to release ~60-nt to 70-nt RNA intermediates that contain individual invader targeting sequences and flanking repeat fragments (Tang, et al. (2002) *Proc. Natl. Acad. Sci. USA* 99:7536-7541; Tang, et al. (2005) *Mol. Microbiol.* 55:469-481; Lillestol, et al. (2006) *Archaea* 2:59-72; Brouns, et al. (2008) *Science* 321:960-964; Hale, et al. (2008) *RNA* 14:2572-2579). In the archaeon *Pyrococcus furiosus*, these intermediate RNAs are further processed to abundant, stable ~35-nt to 45-nt mature psiRNAs (Hale, et al. (2008) supra). The use of the CRISPR/CRISPR-associated (Cas) system for synthetic biology, direct and multiplexed perturbation of gene networks and targeted ex vivo and in vivo gene therapy has been suggested (*Mali*, et al. (2013) *Science* 339:823-6). However, particular molecules for targeting exogenous DNA integrated into the human genome have not been described.

SUMMARY OF THE INVENTION

This invention is a method for inhibiting the function or presence of a target human immunodeficiency virus 1 (HIV-1) DNA sequence in a eukaryotic cell by contacting a eukaryotic cell harboring a target HIV-1 DNA sequence with (a) one or more guide RNA, or nucleic acids encoding said one or more guide RNA, and (b) a Clustered Regularly Interspaced Short Palindromic Repeats-Associated (cas) protein, or nucleic acids encoding said cas protein, wherein said guide RNA hybridizes with said target HIV-1 DNA sequence thereby inhibiting the function or presence of said target HIV-1 DNA sequence. In one embodiment, the target HIV-1 DNA sequence is selected from the group consisting of SEQ ID NO:2-10. In other embodiments, the cas protein is cas9, codon-optimized for expression in human cells and/or includes a nuclear localization sequence.

A kit containing (a) one or more guide RNA, or nucleic acids encoding said one or more guide RNA, wherein said guide RNA hybridizes with a target HIV-1 DNA sequence; and (b) a cas protein; or a nucleic acid encoding said protein is also provided. In one embodiment, the target HIV-1 DNA sequence is selected from the group consisting of SEQ ID NO:2-10. In other embodiments, the cas protein is cas9, codon-optimized for expression in human cells and/or includes a nuclear localization sequence.

A vector harboring nucleic acids encoding one or more guide RNA, wherein said guide RNA hybridizes with a target human immunodeficiency virus 1 DNA sequence selected from the group consisting of SEQ ID NO:2-10 is further provided.

Figure 1:
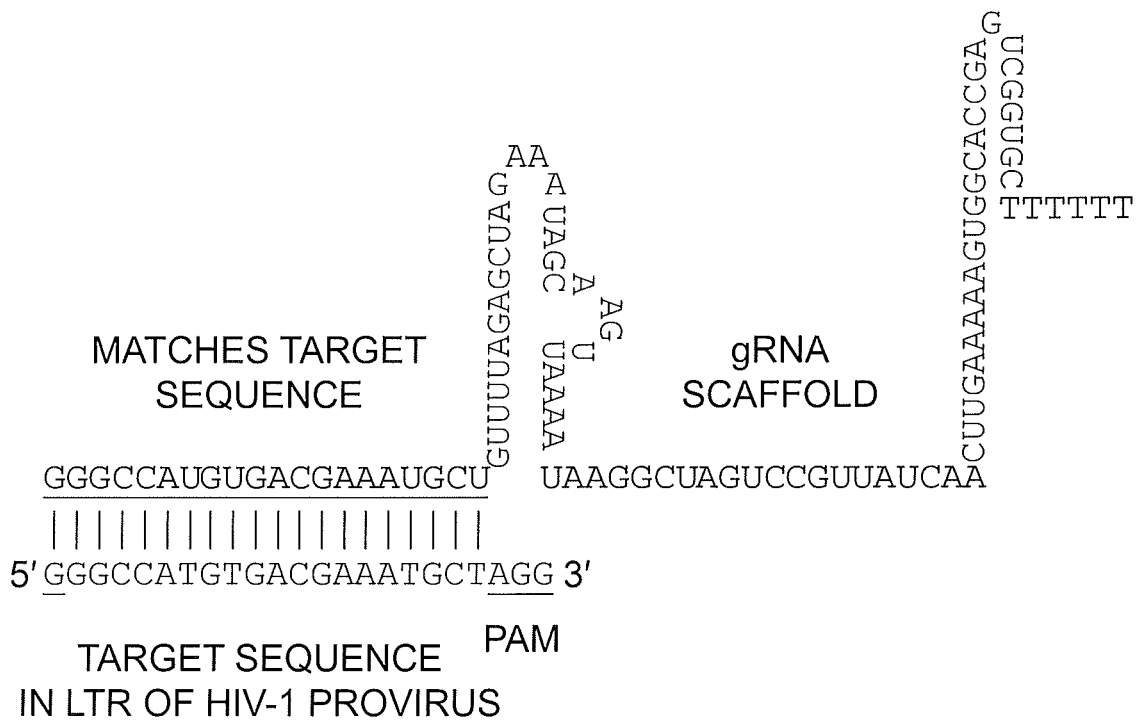
FIG. 1 depicts the secondary structure of a guide RNA transcript with the spacer sequence from HIV-1 LTR. The target sequence in LTR of HIV-1 provirus is SEQ ID NO:3. The top sequence that contains the sequence that matches the target sequence and the gRNA is SEQ ID NO:28.

guide RNA, hCas and HIV-1 reporter plasmid in which an intact LTR and 5' sequence promote the expression of GFP. Total DNA was isolated and assayed for integrity of the recovered reporter plasmid by real-time PCR using primers flanking the binding sites of U3B through GAG guide RNAs.

DETAILED DESCRIPTION OF THE INVENTION

This invention provides methods and kits for using the CRISPR system to interfere with the function and/or presence of segments of human immunodeficiency virus type-1 (HIV-1) DNA, which are integrated into the host cell genome (e.g., located in vitro or in a subject) and are the source of new viral particles. Without this integrated segment of viral DNA, the infected cell cannot produce new viral particles, thus reducing viral burden in an infected person.

Accordingly, this invention is a method for inhibiting the function and/or presence of a target HIV-1 DNA sequence in a eukaryotic cell by administering one or more guide RNA and a cas protein, or nucleic acids encoding said guide RNA or cas protein, to a eukaryotic cell harboring a target HIV-1 DNA sequence, wherein said guide RNA hybridizes with said target HIV-1 DNA sequence thereby interfering with the function and/or presence of said target HIV-1 DNA sequence. The function of an HIV-1 DNA target sequence is inhibited when, e.g., the target sequence is no longer transcribed and/or translated. In this respect, the HIV-1 DNA target can be mutated or excised. The presence of an HIV-1 DNA target sequence is inhibited when the target sequence is, e.g., excised from the host genome.

In bacteria and archaea, the clustered regularly interspaced short palindromic repeats (CRISPR)/CRISPR-associated (Cas) system uses short RNA to direct degradation of foreign nucleic acids (DNA/RNA). CRISPR defense involves acquisition and integration of new targeting "spacers" from invading virus or plasmid DNA into the CRISPR locus, expression and processing of short guiding CRISPR RNAs (crRNAs) composed of spacer-repeat units, and cleavage of nucleic acids (most commonly DNA) complementary to the spacer.

Three classes of CRISPR systems have been described (Type I, II and III). In certain embodiments of this invention, the Type II CRISPR system is employed as it uses a single effector enzyme, Cas9, to cleave dsDNA, whereas Type I and Type III systems require multiple distinct effectors acting as a complex (Makarova, et al. (2011) *Nat. Rev. Microbiol.* 9:467). The Type II effector system is composed of a long pre-crRNA transcribed from the spacer-containing CRISPR locus, the multifunctional Cas9 protein, and a tracrRNA for gRNA processing. The tracrRNAs hybridize to the repeat regions separating the spacers of the pre-crRNA, initiating dsRNA cleavage by endogenous RNase III, which is followed by a second cleavage event within each spacer by Cas9, producing mature crRNAs that remain associated with the tracrRNA and Cas9. However, it has been demonstrated that a tracrRNA:crRNA fusion, termed a guide RNA (gRNA) can function in vitro, obviating the need for RNase III and the crRNA processing in general (Jinek, et al. (2012) *Science* 337:816). Accordingly, in a particular embodiment of this invention, a guide RNA molecule is used to target a HIV-1 DNA sequence. Guide RNA molecules of this invention can range in size from 80 to 130 nucleotides, 90 to 120 nucleotides or 100 to 110 nucleotides in length and be composed of a combination of RNA and DNA. In particular embodiments, the guide RNA has the sequence R-GU UUU AGA GCU AGA AAU AGC AAG UUA AAA UAA GGC UAG UCC GUU AUC AAC UUG AAA AAG UGG CAC CGA GUC GGU GCT TTT TT (SEQ ID NO:1), wherein R is a spacer sequence that specifically hybridizes to an HIV-1 DNA target sequence.

Type II CRISPR interference is a result of Cas9 unwinding the DNA duplex and searching for sequences matching the crRNA to cleave. Target recognition occurs upon detection of complementarity between a "protospacer" sequence in the target DNA and the remaining spacer sequence in the crRNA. Cas9 cuts the DNA only if a correct protospacer-adjacent motif (PAM) is also present at the 3' end. Different Type II systems have differing PAM requirements. The *S. pyogenes* system requires an NGG sequence, where N can be any nucleotide (Mali, et al. (2013) *Science* 339:823-6). *S. thermophilus* Type II systems require NGGNG (Horvath & Barrangou (2010) *Science* 327:167) and NNAGAAW (Deveau, et al. (2008) *J. Bacteriol.* 190:1390), respectively, while different *S. mutans* systems tolerate NGG or NAAR (van der Ploeg, et al. (2009) *Microbiology* 155:1966).

In some embodiments, the guide RNA targets one site in the HIV-1 DNA sequence. In other embodiments, more than one guide RNA is used to target multiple sites within the HIV-1 DNA sequence. In certain embodiments, the spacer of the guide RNA has a target sequence selected from those presented in Table 1. However, bioinformatic analyses have generated extensive databases of CRISPR loci in a variety of bacteria and are of use in determining PAMs and identifying addition CRISPR-targetable HIV-1 sequences (Rho, et al. (2012) *PLoS Genet.* 8:e1002441; Pride, et al. (2011) *Genome Res.* 21:126).

TABLE 1

| Corresponding Region in HIV-1 | Location in Corresponding Region | Guide RNA Target Sequence | SEQ ID NO: |
|---|---|---|---|
| LTR | U3 | TCTACTTGCTCTGGTTCA ACTGG | 2 |
| LTR | U3 | GGGCCATGTGACGAAATG CTAGG | 3 |
| LTR | U3 | CAGCAGTCTTTGTAGTAC TCCGG | 4 |
| LTR | TAR | ACTCAAGGCAAGCTTTAT TGAGG | 5 |
| LTR | U5 | TACCAGAGTCACACAACA GACGG | 6 |
| GAG | 5' UT | GCTGAAGCGCGCACGGCA AGAGG | 7 |
| GAG | N-term | GCGAGAGCGTCGGTATTA AGCGG | 8 |
| GAG | N-term | GAGAGCGTCGGTATTAAG CGGGG | 9 |
| GAG | Coding | GAACGATTCGCAGTTAAT CCTGG | 10 |

LTR, long terminal repeat; u3, a control element; TAR, Tat activating region; U5, a control element; UT, untranslated sequence of Gag; N-term, N-terminal portion of Gag; coding, within protein coding sequence of Gag. Underlined nucleotides indicate a protospacer-adjacent motif (PAM).

In particular embodiments of this invention, the guide RNA targets the LTR portion of the HIV-1 DNA. The LTR functions to promote and regulate the transcription of the genes that are essential for assembling new virions, as well as transcribing the entire HIV-1 genome, which is packaged into infectious particles. There are two copies of the LTR in the integrated provirus, thereby doubling the size of the instant target. The above identified LTR target sequences have the required PAM sequence and are unique to HIV-1, having no cross-reacting homologies in the human genome. This is of particular importance because the human genome contains many other retroviruses with LTR-like sequences. Thus, very low or no cytotoxicity is expected in uninfected cells.

The Type II CRISPR systems include the 'HNH'-type system (Streptococcus-like; also known as the Nmeni subtype, for Neisseria meningitidis serogroup A str. 22491, or CASS4), in which Cas9 is sufficient for generating crRNA and cleaving the target DNA. Cas9 contains at least two nuclease domains, a RuvC-like nuclease domain near the amino terminus and the HNH (or McrA-like) nuclease domain in the middle of the protein. Given that the HNH nuclease domain is abundant in restriction enzymes and possesses endonuclease activity (Kleanthous, et al. (1999) Nat. Struct. Biol. 6:243-52; Jakubauskas, et al. (2007) J. Mol. Biol. 370:157-169), it has been suggested that this domain is responsible for target cleavage. Furthermore, for the S. thermophilus type II CRISPR-Cas system, targeting of plasmid and phage DNA has been demonstrated in vivo (Garneau, et al. (2010) Nature 468:67-71) and inactivation of Cas9 has been shown to abolish interference (Barrangou, et al. (2007) Science 315:1709-12). In some embodiments of this invention, the cas protein used in the cleavage of the HIV-1 target sequence is a Type II cas protein. In other embodiments, the cas protein is a Type II cas protein isolated from Streptococcus thermophilus, Listeria innocua, Neisseria meningitidis or S. pyogenes. In other embodiments, the cas protein is a cas9 protein isolated from Streptococcus thermophilus (See GENBANK Accession No. YP 820832), Listeria innocua (See GENBANK Accession No. NP 472073), Neisseria meningitidis (See GENBANK Accession No. YP 002342100) or S. pyogenes (See GENBANK Accession Nos. AAK33936 and NP 269215). In certain embodiments, the cas9 protein has been codon-optimized for expression in human (SEQ ID NO:11). Plasmids harboring nucleic acids encoding cas9 proteins are available from repository sources such as Addgene (Cambridge, Mass.). Examples of such plasmids include pMJ806 (S. pyogenes cas9), pMJ823 (L. innocua cas9), pMJ824 (S. thermophilus cas9), pMJ839 (N. meningitides cas9), and pMJ920 (human codon-optimized cas9).

To facilitate entry into the nucleus, the cas protein of the invention can include a nuclear localization sequence (NLS). The term "nuclear localization sequence" means an amino acid sequence that induces transport of molecules having such sequences or linked to such sequences into the nucleus of eukaryotic cells. In this context, the term "having" preferably means that the nuclear localization sequence forms part of the molecule, i.e. that it is linked to the remaining parts of the molecule by covalent bonds, e.g., an in-frame protein fusion. The term "linked" in this context means any possible linkage between the nuclear localization sequence and another molecule to be introduced into the nucleus of a eukaryotic cell, e.g., by covalent bonds, hydrogen bonds or ionic interactions. The term "transport into the nucleus" in this context means that the molecule is translocated into the nucleus.

Nuclear translocation can be detected by direct and indirect means. For example, direct observation can be achieved by fluorescence or confocal laser scanning microscopy when the nuclear localization sequence or the translocated molecule (e.g., the cas protein or guide RNA) are labeled with a fluorescent dye (labeling kits are commercially available, e.g., from Pierce or Molecular Probes). Translocation can also be assessed by electron microscopy if the nuclear localization sequence or the translocated molecule (e.g., the cas protein or guide RNA) are labeled with an electron-dense material such as colloidal gold (Oliver (1999) Methods Mol. Biol. 115:341-345). Translocation can be assessed in indirect ways, e.g., by measuring cleavage of a target HIV-1 DNAs sequence.

A number of nuclear localization sequences have been described in the art. These include the nuclear localization sequence of the SV40 virus large T-antigen, the minimal functional unit of which is the seven amino acid sequence PKKKRKV (SEQ ID NO:12). Other examples of nuclear localization sequences include the nucleoplasmin bipartite NLS with the sequence NLSKRPAAIKKAGQAKKKK (SEQ ID NO:13) (Michaud & Goldfarb (1991) J. Cell Biol. 112:215-223), the c-myct nuclear localization sequence having the amino acid sequence PAAKRVKLD (SEQ ID NO:14) or RQRRNELKRSF (SEQ ID NO:15) (Chesky, et al. (1989) Mol. Cell Biol. 9:2487-2492) and the hRNPAI M9 NLS having the sequence NQSSNFGPMKGGNFG-GRSSGPYGGGGQYFAKPRNQGGY (SEQ ID NO:16) (Siomi & Dreyfuss (1995) J. Cell Biol. 129:551-560). Further examples of NLSs include the sequences RMRKFKNKGKDTAELRRRRVEVSVELRKAKKD-EQILKRRNV (SEQ ID NO:17) of the IBB domain from importin-alpha (Gorlich, et al. (1995) Nature 377:246-248); VSRKRPRP (SEQ ID NO:18) and PPKKARED (SEQ ID NO:19) of the myoma T protein; PQPKKKPL (SEQ ID NO:20) from human p53; SALIKKKKKMAP (SEQ ID NO:21) from mouse c-abl IV (Van Etten, et al. (1989) Cell 58:669-678); DRLRR (SEQ ID NO:22) and PKQKKRK (SEQ ID NO:23) from influenza virus NS1 (Greenspan, et al. (1988) J. Virol. 62:3020-3026), RKLKKKIKKL (SEQ ID NO:24) from the Hepatitis virus delta antigen (Chang, et al. (1992) J. Virol. 66:6019-6027); and REKKKFLKRR (SEQ ID NO:25) from the mouse Mxl protein (Zurcher, et al. (1992) J. Virol. 66:5059-5066). It is also possible to use bipartite nuclear localization sequences such as the sequence KRKGDEVDGVDEVAKKKSKK (SEQ ID NO:26) of the human poly(ADP-ribose) polymerase (Schreiber, et al. (1992) EMBO J. 11:3263-3269) or the sequence RKCLQAGMNLEARKTKK (SEQ ID NO:27) of the steroid hormone receptors (human) glucocorticoid (Cadepond, et al. (1992) Exp. Cell Res. 201:99-108). In some embodiments, the NLS is located at the N-terminus of the cas protein. In other embodiments, the NLS is located the C-terminus of the cas protein.

The one or more guide RNA and cas protein can be used in accordance with the methods of this invention as isolated RNA and protein, respectively. As used herein, an isolated molecule (e.g., an isolated nucleic acid such as DNA, RNA or an isolated polypeptide) means a molecule separated or substantially free from at least some of the other components of the naturally occurring organism, such as for example, the cell structural components or other polypeptides or nucleic acids commonly found associated with the molecule. In general, an isolated molecule is at least about 25%, 50%, 60%, 70%, 75%, 80%, 85%, 90%, 95%, 97%, 98%, 99% or more pure (w/w).

Alternatively, the one or more guide RNA and cas protein can be provided to a cell or subject via isolated nucleic acids that encode the guide RNA and cas protein, respectively. In one embodiment, the isolated nucleic acids encoding the guide RNA and cas protein are provided as naked DNA. In another, embodiment, the isolated nucleic acids encoding the guide RNA and cas protein are incorporated into a gene delivery vector. In particular embodiments, the vector is an expression vector. Exemplary vectors include plasmids, lipid vectors and viral vectors. By the term express, expresses or expression of a nucleic acid it is meant that the sequence is transcribed, and in the case of the cas protein, translated thereby resulting in the production of the cas protein.

The methods of the present invention provide a means for delivering, and expressing, nucleic acids encoding a guide RNA and cas protein in human cells. In some embodiments, the nucleic acids are expressed transiently in the target cell. In other embodiments, the nucleic acids are stably incorporated into the target cell, for example, by integration into the genome of the cell or by persistent expression from stably maintained episomes (e.g., derived from Epstein Barr Virus).

As one aspect, the isolated nucleic acids, vectors, methods and kits of the invention find use in a method of administering a guide RNA and cas protein to a subject. In this manner, the guide RNA and cas protein can thus be produced in vivo in the subject. The subject can have, or be at risk of having an HIV-1 infection such that the guide RNA and cas protein impart a therapeutic effect, e.g., reducing viral burden or spread.

It will be apparent to those skilled in the art that any suitable vector can be used to deliver the isolated nucleic acids of this invention to the target cell(s) or subject of interest. The choice of delivery vector can be made based on a number of factors known in the art, including age and species of the target host, level and persistence of expression desired, the target cell or organ, route of delivery, size of the isolated nucleic acid, safety concerns, and the like.

Suitable vectors include virus vectors (e.g., retrovirus, alphavirus; vaccinia virus; adenovirus, adeno-associated virus, or herpes simplex virus), lipid vectors, poly-lysine vectors, synthetic polyamino polymer vectors, plasmids, and the like.

As used herein, the term viral vector or viral delivery vector can refer to a virus particle that functions as a nucleic acid delivery vehicle, and which contains the vector genome packaged within a virion. Alternatively, these terms can be used to refer to the vector genome when used as a nucleic acid delivery vehicle in the absence of the virion.

Protocols for producing recombinant viral vectors and for using viral vectors for nucleic acid delivery can be found in *Current Protocols in Molecular Biology*, Ausubel, F. M. et al. (eds.) Greene Publishing Associates, (1989) and other standard laboratory manuals (e.g., Vectors for Gene Therapy. In: *Current Protocols in Human Genetics*. John Wiley and Sons, Inc.: 1997). Particular examples of viral vectors include, for example, retrovirus, adenovirus, AAV, herpes virus, and poxvirus vectors.

In certain embodiments of this invention, the delivery vector is an adenovirus vector. The term adenovirus, as used herein, is intended to encompass all adenoviruses, including the *Mastadenovirus* and *Aviadenovirus* genera. To date, at least forty-seven human serotypes of adenoviruses have been identified (see, e.g., Fields, et al., Virology, volume 2, chapter 67 (3d ed., Lippincott-Raven Publishers). In one embodiment, the adenovirus is a human serogroup C adenovirus, in another embodiment, the adenovirus is serotype 2 (Ad2) or serotype 5 (Ad5) or simian adenovirus such as AdC68.

Those skilled in the art will appreciate that vectors can be modified or targeted as described in Douglas, et al. (1996) *Nature Biotechnology* 14:1574 and U.S. Pat. Nos. 5,922,315; 5,770,442 and/or 5,712,136.

An adenovirus genome can be manipulated such that it encodes and expresses a nucleic acid of interest but is inactivated in terms of its ability to replicate in a normal lytic viral life cycle. See, for example, Berkner, et al. (1988) *BioTechniques* 6:616; Rosenfeld, et al. (1991) *Science* 252:431-434; and Rosenfeld et al. (1992) *Cell* 68:143-155.

Recombinant adenoviruses can be advantageous in certain circumstances in that they are not capable of infecting nondividing cells and can be used to infect a wide variety of cell types. Furthermore, the virus particle is relatively stable and amenable to purification and concentration, and can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., as occurs with retroviral DNA). Moreover, the carrying capacity of the adenoviral genome for foreign DNA is large relative to other delivery vectors (Haj-Ahmand and Graham (1986) *J. Virol.* 57:267).

In particular embodiments, the adenovirus genome contains a deletion therein, so that at least one of the adenovirus genomic regions does not encode a functional protein. For example, an adenovirus vectors can have E1 genes and packaged using a cell that expresses the E1 proteins (e.g., 293 cells). The E3 region is also frequently deleted as well, as there is no need for complementation of this deletion. In addition, deletions in the E4, E2a, protein IX, and fiber protein regions have been described, e.g., by Armentano, et al. (1997) *J. Virology* 71:2408; Gao, et al. (1996) *J. Virology* 70:8934; Dedieu, et al. (1997) *J. Virology* 71:4626; Wang, et al. (1997) *Gene Therapy* 4:393; U.S. Pat. No. 5,882,877. In general, the deletions are selected to avoid toxicity to the packaging cell. Combinations of deletions that avoid toxicity or other deleterious effects on the host cell can be routinely selected by those skilled in the art.

Those skilled in the art will appreciate that typically, with the exception of the E3 genes, any deletions will need to be complemented in order to propagate (replicate and package) additional virus, e.g., by transcomplementation with a packaging cell.

The present invention can also be practiced with gutted adenovirus vectors (as that term is understood in the art, see e.g., Lieber, et al. (1996) *J. Virol.* 70:8944-60) in which essentially all of the adenovirus genomic sequences are deleted.

Adeno-associated viruses (AAV) have also been employed as nucleic acid delivery vectors. For a review, see Muzyczka, et al. (1992) *Curr. Topics Micro. Immunol.* 158:97-129). AAV are among the few viruses that can integrate their DNA into non-dividing cells, and exhibit a high frequency of stable integration into human chromosome (see, for example, Flotte, et al. (1992) *Am. J. Respir. Cell. Mol. Biol.* 7:349-356; Samulski, et al., (1989) *J Virol.* 63:3822-3828; McLaughlin, et al. (1989) *J. Virol.* 62:1963-1973). A variety of nucleic acids have been introduced into different cell types using AAV vectors (see, for example, Hermonat, et al. (1984) *Proc. Natl. Acad. Sci. USA* 81:6466-6470; Tratschin, et al. (1985) *Mol. Cell. Biol.* 4:2072-2081;

Wondisford, et al. (1988) *Mol. Endocrinol.* 2:32-39; Tratschin, et al. (1984) *J. Virol.* 51:611-619; and Flotte, et al. (1993) *J. Biol. Chem.* 268:3781-3790).

Any suitable method known in the art can be used to produce AAV vectors expressing the nucleic acids of this invention (see, e.g., U.S. Pat. Nos. 5,139,941; 5,858,775; 6,146,874 for illustrative methods). In one particular method, AAV stocks can be produced by co-transfection of a rep/cap vector encoding AAV packaging functions and the template encoding the AAV vDNA into human cells infected with the helper adenovirus (Samulski, et al. (1989) *J. Virology* 63:3822). The AAV rep and/or cap genes can alternatively be provided by a packaging cell that stably expresses the genes (see, e.g., Gao, et al. (1998) *Human Gene Therapy* 9:2353; Inoue, et al. (1998) *J. Virol.* 72:7024; U.S. Pat. No. 5,837,484; WO 98/27207; U.S. Pat. No. 5,658,785; WO 96/17947).

Another vector for use in the present invention is Herpes Simplex Virus (HSV). HSV can be modified for the delivery of nucleic acids to cells by producing a vector that exhibits only the latent function for long-term gene maintenance. HSV vectors are useful for nucleic acid delivery because they allow for a large DNA insert of up to or greater than 20 kilobases; they can be produced with extremely high titers; and they have been shown to express nucleic acids for a long period of time in the central nervous system as long as the lytic cycle does not occur.

In other embodiments of the invention, the delivery vector of interest is a retrovirus. The development of specialized cell lines (termed packaging cells) which produce only replication-defective retroviruses has increased the utility of retroviruses for gene therapy, and defective retroviruses are characterized for use in gene transfer for gene therapy purposes (for a review, see Miller (1990) *Blood* 76:271). A replication-defective retrovirus can be packaged into virions which can be used to infect a target cell through the use of a helper virus by standard techniques.

In addition to viral transfer methods, such as those illustrated above, non-viral methods can also be employed. Many non-viral methods of nucleic acid transfer rely on normal mechanisms used by mammalian cells for the uptake and intracellular transport of macromolecules. In particular embodiments, non-viral nucleic acid delivery systems rely on endocytic pathways for the uptake of the nucleic acid molecule by the targeted cell. Exemplary nucleic acid delivery systems of this type include liposomal-derived systems, poly-lysine conjugates, and artificial viral envelopes.

In particular embodiments, plasmid vectors are used in the practice of this invention. Naked plasmids can be introduced into cells by injection into the tissue. Expression can extend over many months, although the number of positive cells is typically low (Wolff, et al. (1989) *Science* 247:247). Cationic lipids have been demonstrated to aid in introduction of nucleic acids into some cells in culture (Felgner and Ringold (1989) *Nature* 337:387). Injection of cationic lipid plasmid DNA complexes into the circulation of mice has been shown to result in expression of the DNA in lung (Brigham, et al. (1989) *Am. J. Med. Sci.* 298:278). One advantage of plasmid DNA is that it can be introduced into non-replicating cells.

In a representative embodiment, a nucleic acid molecule (e.g., a plasmid) can be entrapped in a lipid particle bearing positive charges on its surface and, optionally, tagged with antibodies against cell-surface antigens of the target tissue (Mizuno, et al. (1992) *No Shinkei Geka* 20:547; WO 91/06309; JP 1047381).

Liposomes that are composed of amphiphilic cationic molecules are useful non-viral vectors for nucleic acid delivery in vitro and in vivo (reviewed in Crystal (1995) *Science* 270:404-410; Blaese, et al. (1995) *Cancer Gene Ther.* 2:291-297; Behr, et al. (1994) *Bioconjugate Chem.* 5:382-389; Remy, et al. (1994) *Bioconjugate Chem.* 5:647-654; and Gao, et al. (1995) *Gene Therapy* 2:710-722). The positively charged liposomes are believed to complex with negatively charged nucleic acids via electrostatic interactions to form lipid:nucleic acid complexes. The lipid:nucleic acid complexes have several advantages as nucleic acid transfer vectors. Unlike viral vectors, the lipid:nucleic acid complexes can be used to transfer expression cassettes of essentially unlimited size. Since the complexes lack proteins, they can evoke fewer immunogenic and inflammatory responses. Moreover, they cannot replicate or recombine to form an infectious agent and have low integration frequency. A number of publications have demonstrated that amphiphilic cationic lipids can mediate nucleic acid delivery in vivo and in vitro (Felgner, et al. (1987) *Proc. Natl. Acad. Sci. USA* 84:7413-17; Loeffler, et al. (1993) *Methods in Enzymology* 217:599-618; Felgner, et al. (1994) *J. Biol. Chem.* 269:2550-2561).

As indicated, the isolated nucleic acids (i.e., encoding guide RNA and a cas protein) can be incorporated into an expression vector (viral or nonviral as described herein). Expression vectors compatible with various host cells are well-known in the art and contain suitable elements for transcription and translation of nucleic acids. Typically, an expression vector contains an expression cassette, which includes, in the 5' to 3' direction, a promoter, a coding sequence encoding one or more guide RNA and/or one or more cas protein operatively associated with the promoter, and, optionally, a termination sequence including a stop signal for RNA polymerase and a polyadenylation signal for polyadenylase. Nucleic acids encoding one or more guide RNA and one or more cas protein can be transcribed as independent molecules (e.g., via independent promoters in independent vectors or the same vector) or on the same molecule, e.g., as bi- or pluri-cistronic mRNA separated by internal ribosomal entry sites (IRESs).

Isolated cas proteins and/or guide RNA, or nucleic acids or vectors encoding said proteins and/or RNA of the invention can be conveniently used or administered in a composition containing the active agents in combination with a carrier. Such compositions can be prepared by methods and contain carriers which are well-known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A carrier, pharmaceutically acceptable carrier, or vehicle, such as a liquid or solid filler, diluent, excipient, or solvent encapsulating material, is involved in carrying or transporting the subject compound from one organ, or portion of the body, to another organ, or portion of the body. Each carrier must be acceptable in the sense of being compatible with the other ingredients of the formulation and not injurious to the patient.

The protein, RNA, nucleic acids or vectors of the invention can be administered via any route including, but not limited to, oral, rectal, topical, buccal (e.g., sub-lingual), vaginal, parenteral (e.g., subcutaneous, intramuscular including skeletal muscle, diaphragm muscle and smooth muscle, intradermal, intravenous, intraperitoneal), topical (i.e., both skin and mucosal surfaces, including airway surfaces), intranasal, transdermal, intraarticular, intrathecal and inhalation administration, administration to the liver by intraportal delivery, as well as direct organ injection. The most suitable route in any given case will depend on the subject being treated and on the nature of the particular molecule which is being used.

Upon administration of one or more guide RNA and cas protein, either isolated or encoded by one or more nucleic acid molecules, to a eukaryotic cell harboring a target HIV-1 DNA sequence, the target HIV-1 DNA sequence is damaged or excised from the genome of the cell and the function of said target HIV-1 DNA sequence is reduced or inhibited. This RNA-directed DNA-targeting via CRISPR interference acts at the DNA level, and therefore differs fundamentally from the RNAi phenomenon observed in eukaryotes and to which CRISPR activity was originally compared (Makarova, et al. (2006) Biol. Direct. 1:7).

Eukaryotic cells of interest in the methods of this invention are preferably mammalian cells, especially HIV-1-positive human immune cells such as helper T cells (specifically CD4$^+$ T cells), macrophages, and dendritic cells. For example, it is contemplated that introduction of the one or more guide RNA and cas protein into the bloodstream of an HIV-1 infected subject will result in transfection of cells in the bloodstream. If a cell is not HIV-1-infected, there will be no damage to the cell as the guiding RNA will not bind. In contrast, if a cell is infected with HIV-1, the guide RNA will hybridize with the target HIV-1 DNA via the spacer sequence, and the cas protein will cleave the target HIV-1 DNA thereby inhibiting the function (e.g., production of new virions/infectious particles) the HIV-1 DNA. In this respect, inhibition of HIV-1 function, using the guide RNA molecules and cas proteins of this invention, is of use in treating or preventing the spread of an HIV-1 infection.

Accordingly, this invention also provides a method for treating or preventing the spread of an HIV-1 infection by administering, to a subject infected by HIV-1, one or more guide RNA and cas protein, or nucleic acid sequences encoding said one or more guide RNA or cas protein, thereby inhibiting the function and/or presence of the HIV-1. The one or more guide RNA and cas protein, or nucleic acids encoding said one or more guide RNA or cas protein, can be administered simultaneously or sequentially. In this respect, the guide RNA or cas proteins (or nucleic acids encoding the same) can be administered in a single formulation or separate formulations. Further, it is contemplated that various combinations of guide RNA and cas proteins can be used. For example, one or more isolated guide RNA molecules can be administered in combination with nucleic acids encoding a cas protein (e.g., in a vector). Alternatively, one or more guide RNA molecules can be administered in a vector in combination with an isolated cas protein. Further, isolated guide RNA molecules can be administered in combination with an isolated cas protein and/or one or more vectors harboring nucleic acids encoding guide RNA molecules can be administered in combination with a vector harboring nucleic acids encoding a cas protein.

Subjects benefiting from such treatment include those identified as being HIV-1-positive as well as subjects at risk of being infected with HIV-1 (e.g., health care workers that may have been exposed to a HIV virus through a needle stick or other patient contact, or patients involved in high-risk activities such as intravenous drug use). Use of the compositions and methods of this invention can decrease viral load and/or prevent the spread of HIV-1 within a subject or from subject to subject.

To facilitate use of the compositions described herein, this invention also provides a kit. The kit contains one or more guide RNA according to the invention, a cas protein as described herein, or nucleic acids encoding the guide RNA or cas protein, e.g., in one or more vectors. In some embodiments, the guide RNA has the sequence as set forth in SEQ ID NO:1. In particular embodiments, the spacer of the guide RNA targets HIV-1 DNA selected from the group of SEQ ID NO:2-10. In another embodiment, the cas protein is a cas9 protein, in particular a human codon-optimized cas9 protein, e.g., as set forth in SEQ ID NO:11. The kit can also include a pharmaceutically acceptable carrier as well as, optionally, technical instructions with information on the administration and dosage of the guide RNA and cas protein invention can be used alone or in combination or concurrently with other conventional HIV treatments including, but not limited to highly active anti-retroviral treatments (HAART), e.g., non-nucleoside reverse transcriptase inhibitors (NNRTIs) such as efavirenz, etravirine and nevirapine; nucleoside reverse transcriptase inhibitors (NRTIs) such as Abacavir, and the combination drugs emtricitabine and tenofovir, and lamivudine and zidovudine; protease inhibitors (PIs) such as atazanavir, darunavir, fosamprenavir and ritonavir; entry or fusion inhibitors such as enfuvirtide and maraviroc; and integrase inhibitors such as raltegravir.

The invention will be further described in the following example, which does not limit the scope of the invention described in the claims.

Example 1

Targeting HIV-1 LTR In Vivo

Figure 2:
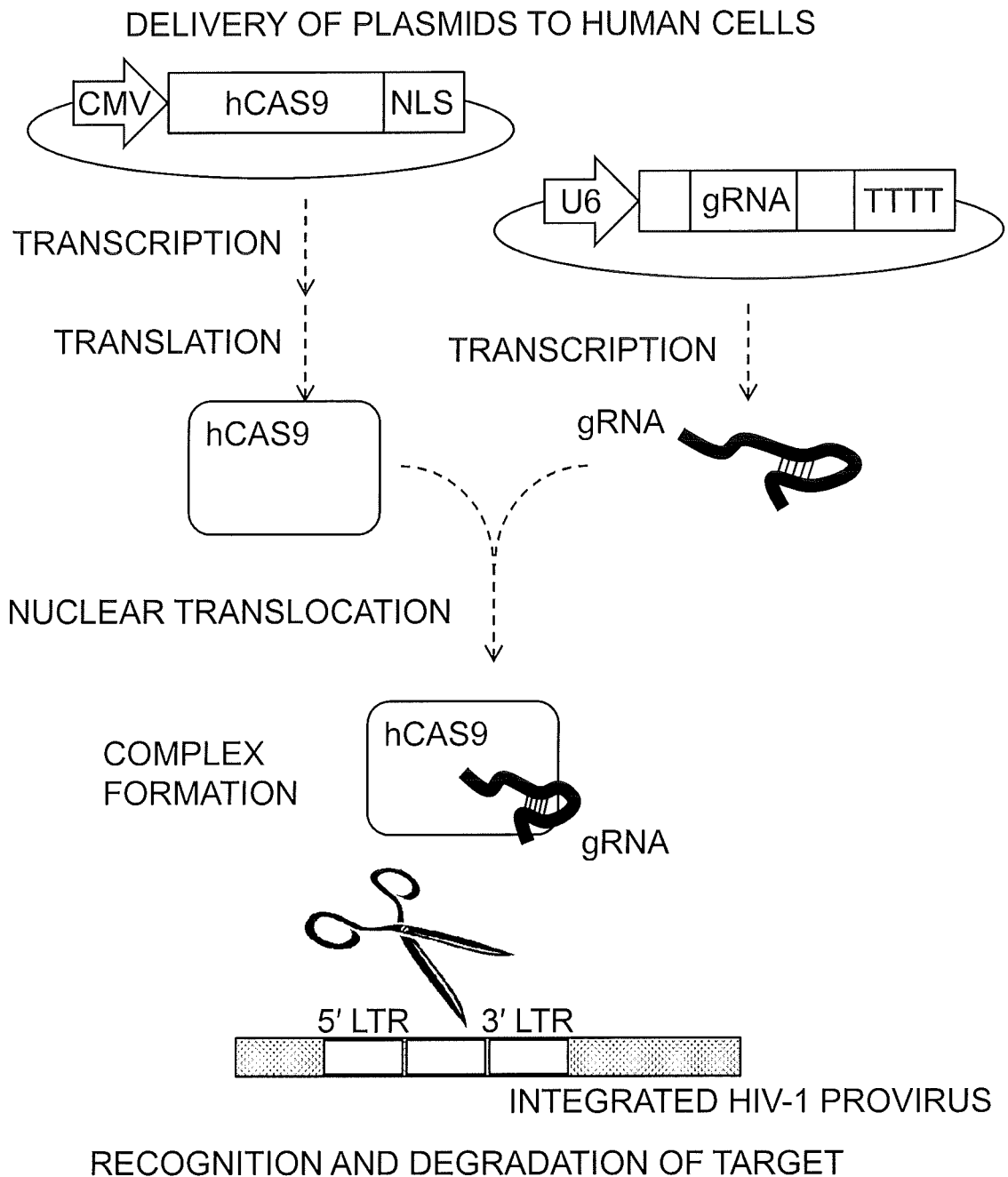
FIG. 2 shows the delivery of the guide RNA (gRNA) and cas protein with subsequent transcription, translation and cleavage of the HIV-1 target sequence.

Plasmid DNA encoding the guiding RNA molecule that uniquely binds to one of five specific regions located within the HIV-1 long terminal repeat region of the HIV-1 proviral DNA is generated (FIG. 1). Likewise, a plasmid encoding a cas9 nuclease is generated. Both plasmids are delivered to human cells, where the cas9 and guiding RNA loci are transcribed and the cas9 transcript is translated. Subsequently, the guiding RNA segment binds the cas9 nuclease to form a hybrid complex. Because of the addition of a nuclear localization sequence, this hybrid complex enters the nucleus where the guiding RNA segment binds to its complementary sequence in the HIV-1 proviral DNA. The nuclease cuts the proviral DNA, effecting a double-stranded DNA cut that is generally not repairable. See FIG. 2. Using this method, HIV-1 proviral DNA can be excised from the genome of an infected cell.

Example 2

Use of CRISPR/Cas to Target Integrated HIV-1 LTR in J-Lat Cells

Using a J-Lat cell line (a human T cell cancer line), it was determined whether cleavage of the HIV-1 Long Terminal Repeat (LTR) region by the guide RNA:hCas9 complex alters the transcriptional activity of these cells. Flow cytometry was used to quantify cells that produce green fluorescent protein (GFP) from the LTR promoter 22 hours after transfection. Flow cytometry analysis provides both a percentage of cells that express GFP and allows the quantification of the intensity of expression within the cell population by quantifying the mean fluorescence intensity (MFI) of the GFP+ cells. Flow cytometry can distinguish between mutations in the LTR region that reduce transcription from those that completely abolish it.

Figure 3A:
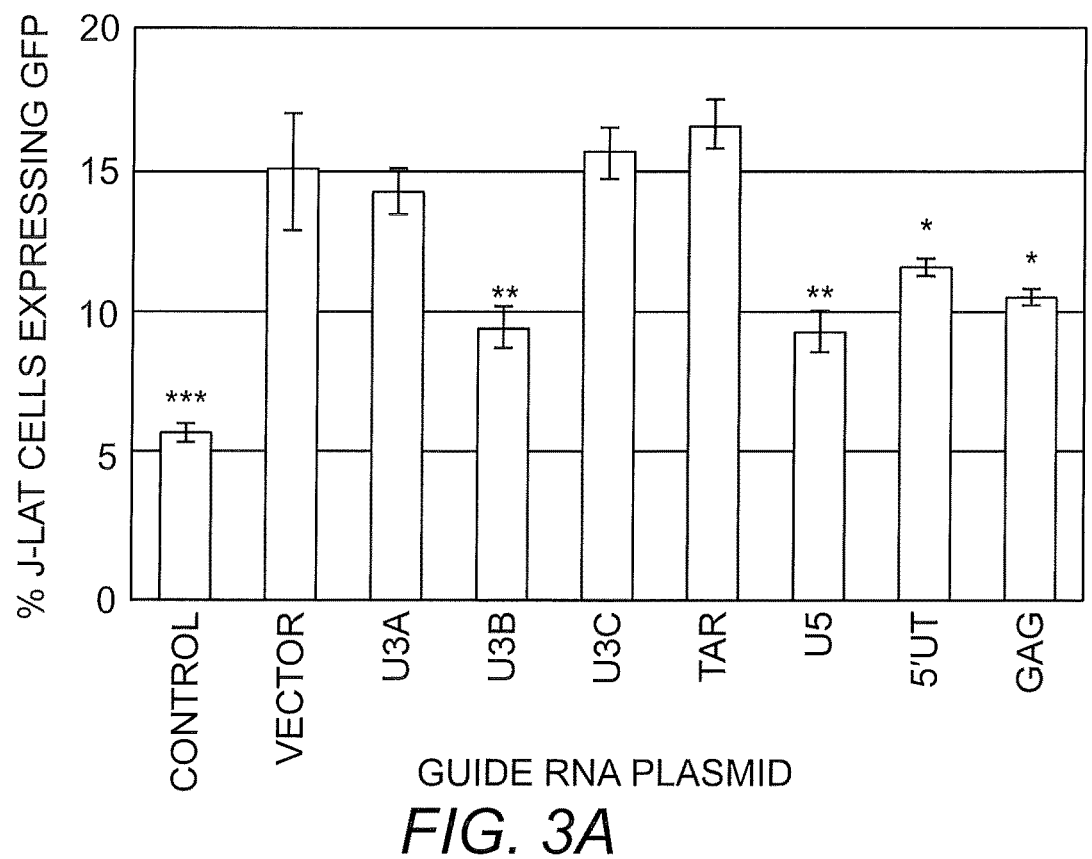
FIG. 3A shows the effect of HIV-specific guide RNA and hCas9 expression on the expression of endogenous LTR promoter-driven GFP expression. Transfection of an empty vector modestly activates expression of GFP (15% GFP+ cells versus 6% GFP+ cells in untreated controls). Co-transfection of hCas expression plasmid and the indicated guide RNA expression plasmids (U3A, U3B, U3C, TAR, U5, 5'UT, and GAG) in some cases (most notably U3B and U5) reduced the expression to below 10%, whereas other guide RNAs had no effect (e.g., U3A, U3C and TAR). All transfections were performed in triplicate. ANOVA statistics indicate significant differences between the empty vector and some guide RNAs with *p=<0.05; p=<0.005; *p=<0.0005.
Figure 3B:
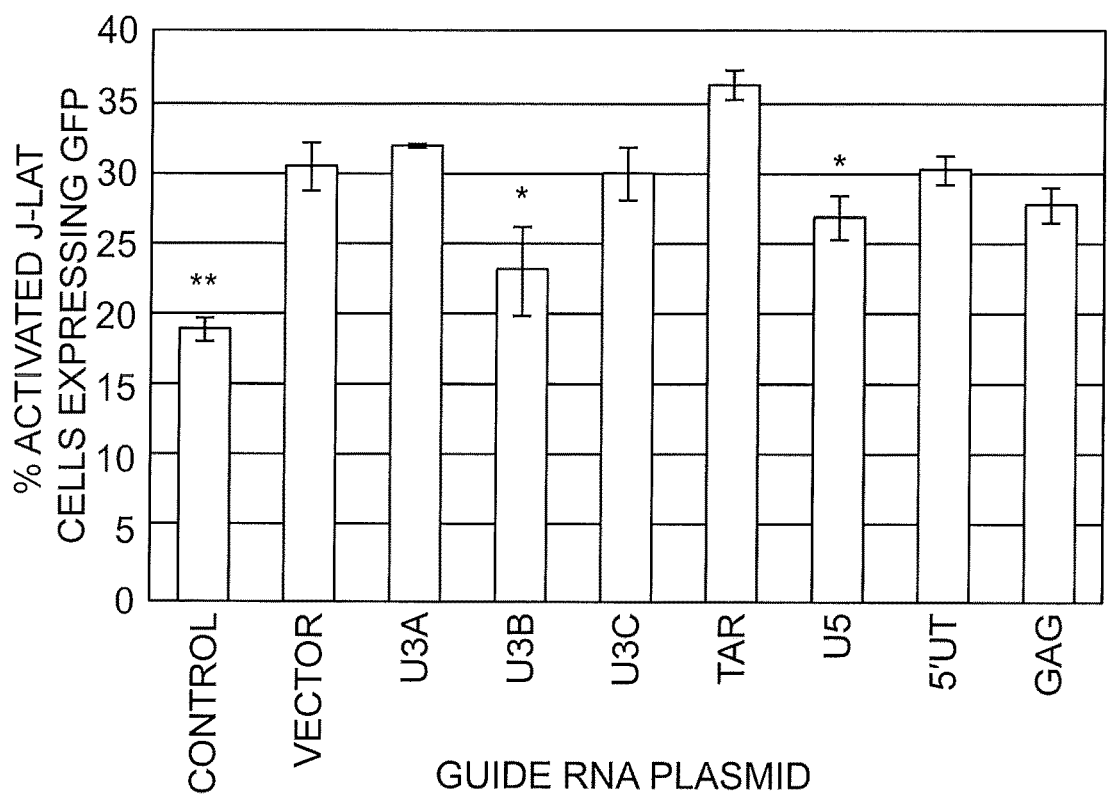
FIG. 3B shows the effect of HIV-specific guide RNA and hCas9 expression on the expression of endogenous LTR promoter-driven GFP expression in the presence of TNF-α. This analysis indicated that moderate activation of J-Lat cells with exposure to 5 ng/ml TNF-α for only six hours did not alter the results presented in FIG. 3A, indicating durable alterations in the integrity of the LTR resulting from specific guide RNA-guided cleavage. All transfections were performed in triplicate. ANOVA statistics indicate significant differences between the empty vector and some guide RNAs with *p=<0.05; p=<0.005; *p=<0.0005.

For this analysis, J-Lat cells were co-transfected with HIV-specific guide RNAs recognizing several different regions within the integrated provirus as described herein, along with the plasmid encoding hCas9. As shown in FIGS. 3A and 3B, guide RNAs to the U3B and U5 regions of the LTR were the most effective in reducing GFP expression (indicating a disruption in the HIV-1 LTR), whereas those to the U3A, U3C and TAR regions were relatively ineffective. In addition to demonstrating the ability of the CRISPR/Cas to target the HIV-1 LTR in a human cell line, these data also underscore the utility of this cell line in providing a rapid readout of guide RNA efficacy.

Example 3

CRISPR/Cas Method for Cleave HIV-1 DNA Expressed by Plasmid DNA

To determine the efficacy of the CRISPR/Cas method to cleave within the HIV-1 LTR and alter transcription, Jurkat cells were transfected with three different plasmids. These plasmids included various guide RNAs, the humanized Cas9 plasmid, and a third (reporter) plasmid in which an intact HIV-1 LTR and 5' sequences promote the expression of GFP.

Figure 4A:
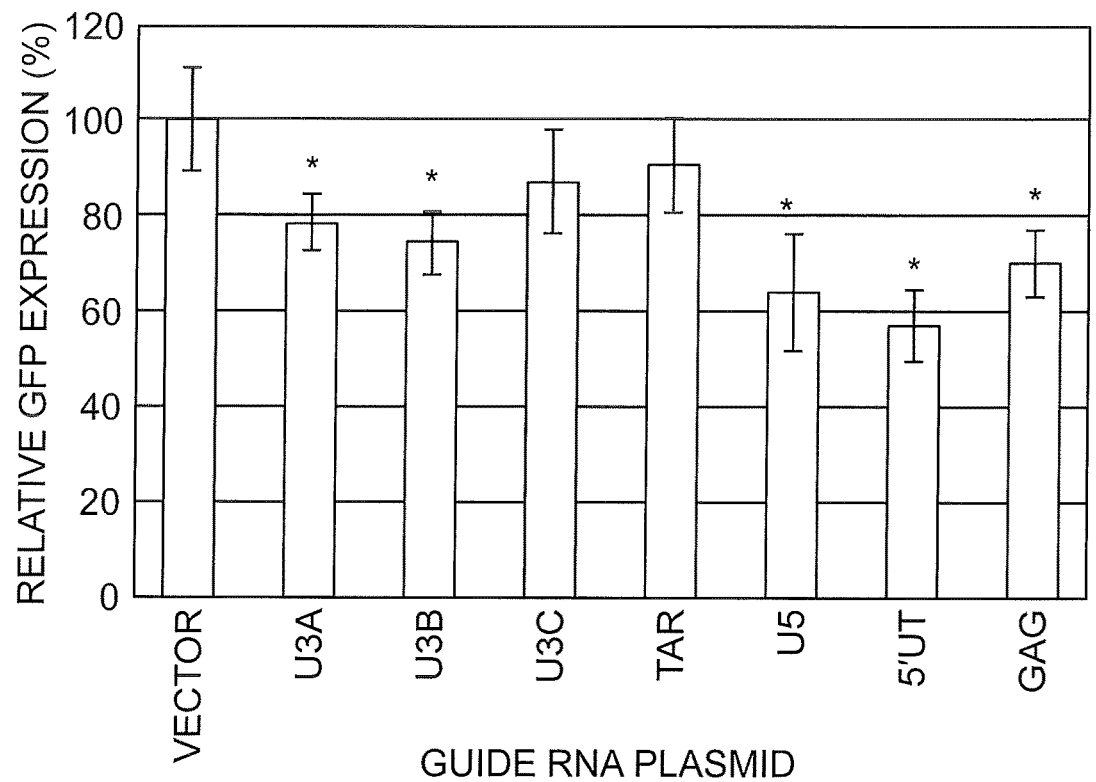
FIG. 4A shows that specific guide RNA reduce GFP expression from a LTR reporter plasmid. Jurkat cells were transfected with three plasmids: guide RNA, hCas and HIV-1 reporter plasmid in which an intact LTR and 5' sequence promote the expression of GFP. The results show a reduction in the percent of cells expressing GFP with several guide RNA plasmids, but not with guide RNA to U3C and TAR. The graph represents the compilation of two separate experiments each with triplicate wells, *p=<0.05.
Figure 4B:
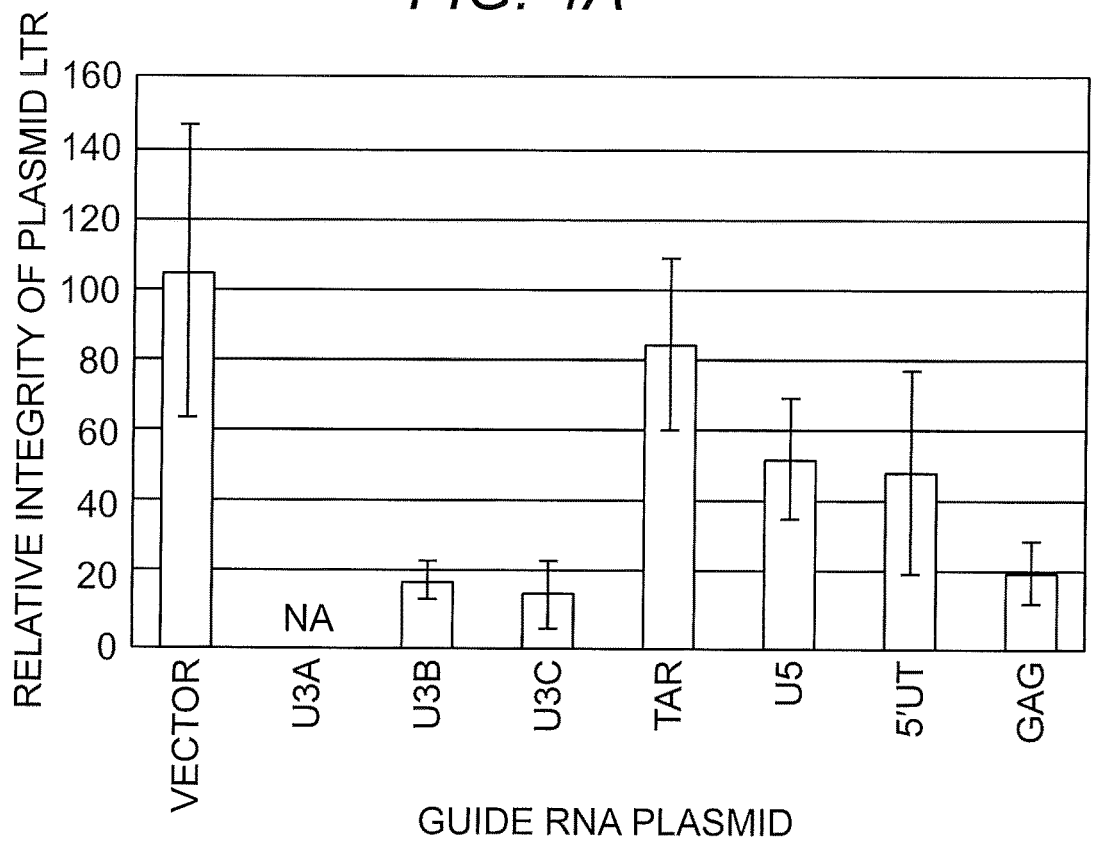
FIG. 4B shows the relative integrity of reporter plasmid LTR. Jurkat cells were transfected with three plasmids.

As shown in FIG. 4A, the use of guide RNAs to the U3A, U3B and U5 regions in the LTR significantly reduced expression of GFP from the reporter plasmid in transfected Jurkat cells. This confirmed the results observed in J-Lat cells (FIGS. 3A and 3B). Interestingly, guide RNAs to the 5' untranslated region immediately downstream from the LTR (5'Untranslated region (UT) and to the gag (group antigen) region (GAG)), also reduced GFP expression from the reporter plasmid. The cells were subsequently lysed to recover the DNA and polymerase chain reaction was performed using primers to the reporter plasmid that would amplify a region from U3B through GAG (and hence not amplify the U3A region). The preliminary data (FIG. 4B) indicated that the integrity of the reporter plasmid was compromised (cleaved) in transfections that included guide RNAs to U3B, U3C, GAG, and likely also to the U5 and 5'UT region, but not to TAR (a regulatory region in the HIV-1 provirus). Thus, this reporter plasmid is also of use in quickly screening guide RNAs.

What is claimed is:

1. A method for inhibiting the function or presence of a target human immunodeficiency virus 1 (HIV-1) DNA sequence in a eukaryotic cell comprising contacting a eukaryotic cell comprising a cellular genome and harboring a target HIV-1 DNA sequence integrated into the cellular genome with
   (a) one or more guide RNA, or nucleic acids encoding said one or more guide RNA, and
   (b) a Clustered Regularly Interspaced Short Palindromic Repeats-Associated 9 (cas9) protein, or nucleic acids encoding said cas9 protein,
   wherein said one or more guide RNA matches said target HIV-1 DNA sequence and uniquely hybridizes to a complementary sequence of the target HIV-1 DNA sequence, thereby inhibiting the function or presence of said target HIV-1 DNA sequence,
   wherein said target HIV-1 DNA sequence is selected from the group consisting of SEQ ID NO:3, SEQ ID NO:6, and SEQ ID NO:4.

2. The method of claim 1, wherein said one or more guide RNA and said cas9 protein form a complex inside the eukaryotic cell, and wherein said complex cuts the HIV-1 DNA sequence, thereby inhibiting the function or presence of said target HIV-1 DNA sequence.

3. The method of claim 2, wherein the one or more guide RNA target an HIV-1 LTR sequence selected from the complement of SEQ ID NO:3 or SEQ ID NO:6.

4. The method of claim 3, wherein said target HIV-1 LTR sequence is SEQ ID NO:3, and wherein said one or more guide RNA, or nucleic acids encoding said one or more guide RNA comprise the sequence of SEQ ID NO:3.

5. The method of claim 3, wherein said target HIV-1 LTR sequence is SEQ ID NO:6, and wherein said one or more guide RNA, or nucleic acids encoding said one or more guide RNA comprise the sequence of SEQ ID NO:6.

6. The method of claim 1, wherein the cas protein has been codon-optimized for expression in human cells.

7. The method of claim 1, wherein the cas protein further comprises a nuclear localization sequence.

8. The method of claim 1, wherein said nucleic acids encoding said one or more guide RNA, and said nucleic acids encoding said cas protein are contained in a viral vector, and wherein contacting said eukaryotic cell comprises contacting with said viral vector.

9. The method of claim 1, wherein the contacting step is carried out in vitro.

10. The method of claim 1, further comprising contacting the eukaryotic cell with one or more guide RNA, or nucleic acids encoding a guide RNA, wherein the guide RNA or nucleic acid encoding a guide RNA matches said target HIV-1 DNA sequence and uniquely hybridizes to a complementary sequence of the target HIV-1 DNA sequence, wherein said target HIV-1 DNA sequence is selected from the group consisting of SEQ ID NO:7, SEQ ID NO:8, and SEQ ID NO:9.

* * * * *

SEQUENCE LISTING

```
<160> NUMBER OF SEQ ID NOS: 28

<210> SEQ ID NO 1
<211> LENGTH: 82
<212> TYPE: DNA
<213> ORGANISM: Artificial Sequence
<220> FEATURE:
<223> OTHER INFORMATION: Synthetic oligonucleotide

<400> SEQUENCE: 1
guuuuagagc uagaaauagc aaguuaaaau aaggcuaguc cguuaucaac uugaaaaagu      60
ggcaccgagu cggugcttt tt                                                82

<210> SEQ ID NO 2
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 2
tctacttgct ctggttcaac tgg                                              23

<210> SEQ ID NO 3
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 3
gggccatgtg acgaaatgct agg                                              23

<210> SEQ ID NO 4
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 4
cagcagtctt tgtagtactc cgg                                              23
```

<210> SEQ ID NO 5
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 5
actcaaggca agctttattg agg                                        23

<210> SEQ ID NO 6
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 6
taccagagtc acacaacaga cgg                                        23

<210> SEQ ID NO 7
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 7
gctgaagcgc gcacggcaag agg                                        23

<210> SEQ ID NO 8
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 8
gcgagagcgt cggtattaag cgg                                        23

<210> SEQ ID NO 9
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 9
gagagcgtcg gtattaagcg ggg                                        23

<210> SEQ ID NO 10
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 10
gaacgattcg cagttaatcc tgg                                        23

<210> SEQ ID NO 11
<211> LENGTH: 1368
<212> TYPE: PRT
<213> ORGANISM: Artificial sequence
<220> FEATURE:
<223> OTHER INFORMATION: Synthetic polypeptide

<400> SEQUENCE: 11

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
            35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65              70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
                115                 120                 125

His Glu Lys Tyr Pro Thr Ile Tyr His Leu Arg Lys Lys Leu Val Asp
                130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
                195                 200                 205

Lys Ala Ile Leu Ser Ala Arg Leu Ser Lys Ser Arg Arg Leu Glu Asn
                210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
                275                 280                 285

Leu Phe Leu Ala Ala Lys Asn Leu Ser Asp Ala Ile Leu Leu Ser Asp
                290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
                370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
```

```
                    405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
            435                 440                 445
Pro Tyr Tyr Val Gly Pro Leu Ala Arg Gly Asn Ser Arg Phe Ala Trp
            450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
            485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
            530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
            565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
            595                 600                 605
Asn Glu Glu Asn Glu Asp Ile Leu Glu Asp Ile Val Leu Thr Leu Thr
            610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
            645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
            675                 680                 685
Ala Asn Arg Asn Phe Met Gln Leu Ile His Asp Asp Ser Leu Thr Phe
            690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
            725                 730                 735
Ile Leu Gln Thr Val Lys Val Val Asp Glu Leu Val Lys Val Met Gly
            740                 745                 750
Arg His Lys Pro Glu Asn Ile Val Ile Glu Met Ala Arg Glu Asn Gln
            755                 760                 765
Thr Thr Gln Lys Gly Gln Lys Asn Ser Arg Glu Arg Met Lys Arg Ile
            770                 775                 780
Glu Glu Gly Ile Lys Glu Leu Gly Ser Gln Ile Leu Lys Glu His Pro
785                 790                 795                 800
Val Glu Asn Thr Gln Leu Gln Asn Glu Lys Leu Tyr Leu Tyr Tyr Leu
            805                 810                 815
Gln Asn Gly Arg Asp Met Tyr Val Asp Gln Glu Leu Asp Ile Asn Arg
            820                 825                 830
```

```
Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
            930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
        1010                1015                1020

Lys Ser Glu Gln Glu Ile Gly Lys Ala Thr Ala Lys Tyr Phe Phe
        1025                1030                1035

Tyr Ser Asn Ile Met Asn Phe Phe Lys Thr Glu Ile Thr Leu Ala
        1040                1045                1050

Asn Gly Glu Ile Arg Lys Arg Pro Leu Ile Glu Thr Asn Gly Glu
        1055                1060                1065

Thr Gly Glu Ile Val Trp Asp Lys Gly Arg Asp Phe Ala Thr Val
        1070                1075                1080

Arg Lys Val Leu Ser Met Pro Gln Val Asn Ile Val Lys Lys Thr
        1085                1090                1095

Glu Val Gln Thr Gly Gly Phe Ser Lys Glu Ser Ile Leu Pro Lys
        1100                1105                1110

Arg Asn Ser Asp Lys Leu Ile Ala Arg Lys Lys Asp Trp Asp Pro
        1115                1120                1125

Lys Lys Tyr Gly Gly Phe Asp Ser Pro Thr Val Ala Tyr Ser Val
        1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
        1160                1165                1170

Phe Glu Lys Asn Pro Ile Asp Phe Leu Glu Ala Lys Gly Tyr Lys
        1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
        1205                1210                1215

Glu Leu Gln Lys Gly Asn Glu Leu Ala Leu Pro Ser Lys Tyr Val
        1220                1225                1230
```

Asn Phe Leu Tyr Leu Ala Ser His Tyr Glu Lys Leu Lys Gly Ser
               1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 12
<211> LENGTH: 7
<212> TYPE: PRT
<213> ORGANISM: Artificial sequence
<220> FEATURE:
<223> OTHER INFORMATION: Synthetic peptide

<400> SEQUENCE: 12

Pro Lys Lys Lys Arg Lys Val
1               5

<210> SEQ ID NO 13
<211> LENGTH: 19
<212> TYPE: PRT
<213> ORGANISM: Artificial sequence
<220> FEATURE:
<223> OTHER INFORMATION: Synthetic peptide

<400> SEQUENCE: 13

Asn Leu Ser Lys Arg Pro Ala Ala Ile Lys Lys Ala Gly Gln Ala Lys
1               5                   10                  15

Lys Lys Lys

<210> SEQ ID NO 14
<211> LENGTH: 9
<212> TYPE: PRT
<213> ORGANISM: Artificial sequence
<220> FEATURE:
<223> OTHER INFORMATION: Synthetic peptide

<400> SEQUENCE: 14

Pro Ala Ala Lys Arg Val Lys Leu Asp
1               5

<210> SEQ ID NO 15
<211> LENGTH: 11
<212> TYPE: PRT
<213> ORGANISM: Artificial sequence
<220> FEATURE:
<223> OTHER INFORMATION: Synthetic peptide

<400> SEQUENCE: 15

Arg Gln Arg Arg Asn Glu Leu Lys Arg Ser Phe

```
<210> SEQ ID NO 16
<211> LENGTH: 38
<212> TYPE: PRT
<213> ORGANISM: Artificial sequence
<220> FEATURE:
<223> OTHER INFORMATION: Synthetic peptide

<400> SEQUENCE: 16

Asn Gln Ser Ser Asn Phe Gly Pro Met Lys Gly Gly Asn Phe Gly Gly
1               5                   10                  15
Arg Ser Ser Gly Pro Tyr Gly Gly Gly Gln Tyr Phe Ala Lys Pro
            20                  25                  30
Arg Asn Gln Gly Gly Tyr
        35

<210> SEQ ID NO 17
<211> LENGTH: 41
<212> TYPE: PRT
<213> ORGANISM: Artificial sequence
<220> FEATURE:
<223> OTHER INFORMATION: Synthetic peptide

<400> SEQUENCE: 17

Arg Met Arg Lys Phe Lys Asn Lys Gly Lys Asp Thr Ala Glu Leu Arg
1               5                   10                  15
Arg Arg Arg Val Glu Val Ser Val Glu Leu Arg Lys Ala Lys Lys Asp
            20                  25                  30
Glu Gln Ile Leu Lys Arg Arg Asn Val
        35                  40

<210> SEQ ID NO 18
<211> LENGTH: 8
<212> TYPE: PRT
<213> ORGANISM: Artificial sequence
<220> FEATURE:
<223> OTHER INFORMATION: Synthetic peptide

<400> SEQUENCE: 18

Val Ser Arg Lys Arg Pro Arg Pro
1               5

<210> SEQ ID NO 19
<211> LENGTH: 8
<212> TYPE: PRT
<213> ORGANISM: Artificial sequence
<220> FEATURE:
<223> OTHER INFORMATION: Synthetic peptide

<400> SEQUENCE: 19

Pro Pro Lys Lys Ala Arg Glu Asp
1               5

<210> SEQ ID NO 20
<211> LENGTH: 8
<212> TYPE: PRT
<213> ORGANISM: Artificial sequence
<220> FEATURE:
<223> OTHER INFORMATION: Synthetic peptide

<400> SEQUENCE: 20

Pro Gln Pro Lys Lys Lys Pro Leu
1               5
```

<210> SEQ ID NO 21
<211> LENGTH: 12
<212> TYPE: PRT
<213> ORGANISM: Artificial sequence
<220> FEATURE:
<223> OTHER INFORMATION: Synthetic peptide

<400> SEQUENCE: 21

Ser Ala Leu Ile Lys Lys Lys Lys Lys Met Ala Pro
1               5                   10

<210> SEQ ID NO 22
<211> LENGTH: 5
<212> TYPE: PRT
<213> ORGANISM: Artificial sequence
<220> FEATURE:
<223> OTHER INFORMATION: Synthetic peptide

<400> SEQUENCE: 22

Asp Arg Leu Arg Arg
1               5

<210> SEQ ID NO 23
<211> LENGTH: 7
<212> TYPE: PRT
<213> ORGANISM: Artificial sequence
<220> FEATURE:
<223> OTHER INFORMATION: Synthetic peptide

<400> SEQUENCE: 23

Pro Lys Gln Lys Lys Arg Lys
1               5

<210> SEQ ID NO 24
<211> LENGTH: 10
<212> TYPE: PRT
<213> ORGANISM: Artificial sequence
<220> FEATURE:
<223> OTHER INFORMATION: Synthetic peptide

<400> SEQUENCE: 24

Arg Lys Leu Lys Lys Lys Ile Lys Lys Leu
1               5                   10

<210> SEQ ID NO 25
<211> LENGTH: 10
<212> TYPE: PRT
<213> ORGANISM: Artificial sequence
<220> FEATURE:
<223> OTHER INFORMATION: Synthetic peptide

<400> SEQUENCE: 25

Arg Glu Lys Lys Lys Phe Leu Lys Arg Arg
1               5                   10

<210> SEQ ID NO 26
<211> LENGTH: 20
<212> TYPE: PRT
<213> ORGANISM: Artificial sequence
<220> FEATURE:
<223> OTHER INFORMATION: Synthetic peptide

<400> SEQUENCE: 26

Lys Arg Lys Gly Asp Glu Val Asp Gly Val Asp Glu Val Ala Lys Lys
1               5                   10                  15

Lys Ser Lys Lys

```
<210> SEQ ID NO 27
<211> LENGTH: 17
<212> TYPE: PRT
<213> ORGANISM: Artificial sequence
<220> FEATURE:
<223> OTHER INFORMATION: Synthetic peptide

<400> SEQUENCE: 27

Arg Lys Cys Leu Gln Ala Gly Met Asn Leu Glu Ala Arg Lys Thr Lys
1               5                   10                  15

Lys

<210> SEQ ID NO 28
<211> LENGTH: 102
<212> TYPE: DNA
<213> ORGANISM: Artificial Sequence
<220> FEATURE:
<223> OTHER INFORMATION: synthetic construct; gRNA

<400> SEQUENCE: 28
gggccaugug acgaaaugcu guuuuagagc uagaaauagc aaguuaaaau aaggcuaguc        60
cguuaucaac uugaaaaagu ggcaccgagu cggugcttttt tt                         102
```